(12) United States Patent
Preissman

(10) Patent No.: US 10,925,661 B2
(45) Date of Patent: Feb. 23, 2021

(54) ELECTROSURGICAL CUTTER LIGHTING AND SUCTION SYSTEMS

(71) Applicant: KELLER MEDICAL, INC., Stuart, FL (US)

(72) Inventor: Howard E. Preissman, Stuart, FL (US)

(73) Assignee: KELLER MEDICAL, INC., Stuart, FL (US)

(*) Notice: Subject to any disclaimer, the term of this patent is extended or adjusted under 35 U.S.C. 154(b) by 260 days.

(21) Appl. No.: 15/885,314

(22) Filed: Jan. 31, 2018

(65) Prior Publication Data

US 2018/0153635 A1 Jun. 7, 2018

Related U.S. Application Data

(63) Continuation of application No. PCT/US2016/047423, filed on Aug. 17, 2016.

(60) Provisional application No. 62/206,688, filed on Aug. 18, 2015.

(51) Int. Cl.
*A61B 18/14* (2006.01)
*A61B 90/35* (2016.01)
*A61B 18/00* (2006.01)

(52) U.S. Cl.
CPC .......... *A61B 18/1402* (2013.01); *A61B 90/35* (2016.02); *A61B 2018/00601* (2013.01); *A61B 2018/1412* (2013.01)

(58) Field of Classification Search
CPC ............... A61B 17/32; A61B 17/3209; A61B 17/32093; A61B 17/3211; A61B 2017/32113; A61B 18/14; A61B 18/1402; A61B 2018/1405; A61B 2018/1412; A61B 2018/00571; A61B 2018/00601
See application file for complete search history.

(56) References Cited

U.S. PATENT DOCUMENTS

| | | | | |
|---|---|---|---|---|
| 5,035,695 A | * | 7/1991 | Weber, Jr. | A61B 18/1402 604/35 |
| 5,314,406 A | * | 5/1994 | Arias | A61M 3/0233 604/21 |
| 5,665,085 A | * | 9/1997 | Nardella | A61B 17/07207 227/180.1 |
| 2011/0238053 A1 | * | 9/2011 | Brannan | A61B 17/3211 606/33 |
| 2012/0221000 A1 | * | 8/2012 | Bromley | A61B 18/1402 606/41 |
| 2012/0259324 A1 | * | 10/2012 | Brannan | A61B 17/3211 606/33 |
| 2013/0345695 A1 | * | 12/2013 | McPherson | A61B 18/1477 606/34 |
| 2014/0066928 A1 | * | 3/2014 | Bennett | A61B 17/32002 606/45 |
| 2014/0276763 A1 | * | 9/2014 | Greep | A61B 18/1402 606/34 |
| 2015/0216618 A1 | | 8/2015 | Jayaraj | |
| 2016/0213415 A1 | * | 7/2016 | Carter | A61B 17/3421 |

(Continued)

OTHER PUBLICATIONS

WO, PCT/US2016/047423 ISR and Written Opinion, dated Oct. 27, 2016.

*Primary Examiner* — Eric S Gibson
(74) *Attorney, Agent, or Firm* — One LLP

(57) ABSTRACT

Electrosurgical cutter or knife lighting and/or suction devices, systems and methods are described. The lighting features and suction features may be variously employed together or alone.

21 Claims, 4 Drawing Sheets

(56) References Cited

U.S. PATENT DOCUMENTS

| | | | |
|---|---|---|---|
| 2016/0278874 A1* | 9/2016 | Fleenor | A61B 90/30 |
| 2018/0153635 A1* | 6/2018 | Preissman | A61B 18/1402 |
| 2019/0142502 A1* | 5/2019 | Batchelor | A61B 17/285 |

* cited by examiner

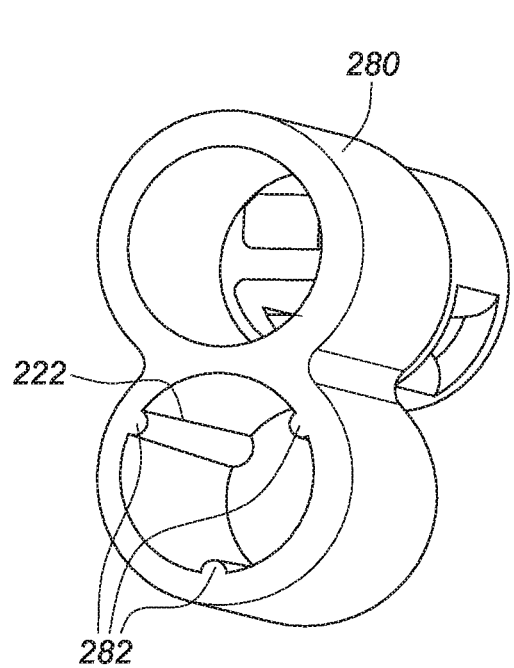 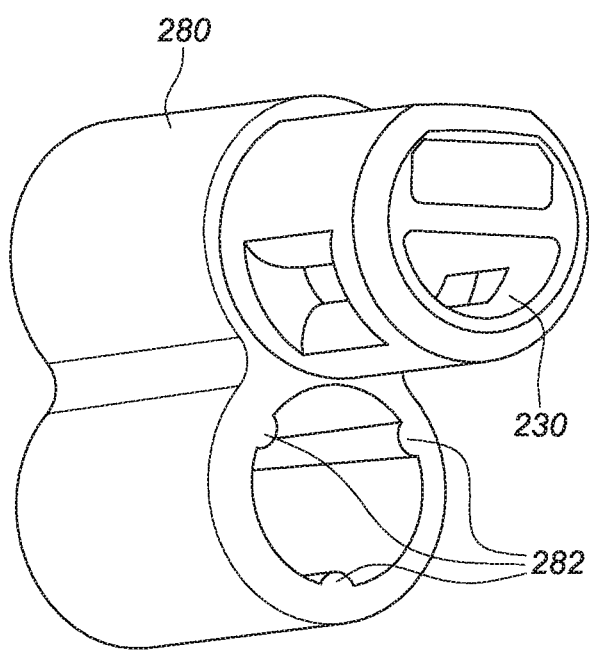
FIG. 4A    FIG. 4B
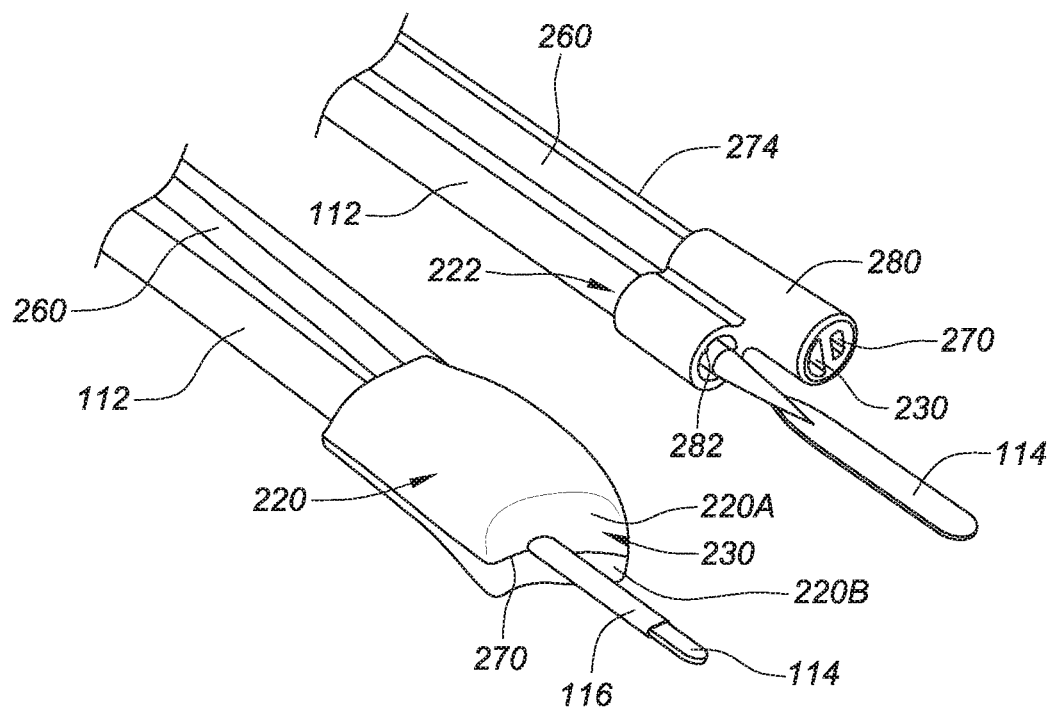
FIG. 5

ELECTROSURGICAL CUTTER LIGHTING AND SUCTION SYSTEMS

CROSS-REFERENCE TO RELATED APPLICATIONS

The subject application is a continuation of PCT Patent Application No. PCT/US16/47423, filed Aug. 17, 2016, which claims priority to U.S. Provisional Patent Application No. 62/206,688, filed on Aug. 18, 2015, both of which are incorporated by reference herein in their entirety for all purposes.

FIELD

The embodiments described herein relate to surgical instruments, particularly ancillary or adjunct components to electrosurgical cutters and associated systems.

BACKGROUND

The LUMIPEN device (shown in FIGS. 1A-1C) is a device that clips onto a electrosurgical cutter or knife handle. The LUMIPEN was designed to provide light in a surgical pocket when cutting.

In a medical procedure, operating room (OR) light is typically provided from ceiling mounted overhead fixtures, headlamps worn by surgeon, or a fixture attached to a retractor. These approaches have drawbacks in that it can be difficult to pass light into the surgical pocket and it can be difficult to avoid instruments obstruct the light when interposed between the light source and the region in need of visualization. The LUMIPEN addresses these limitations by placing a light source at a distal limit of an electrosurgical cutter or electrocautery handle.

Embodiments hereof improve upon the LUMIPEN in a number of ways. These options are treated in turn with further reference to the LUMIPEN, although the embodiments are not limited to use with the LUMIPEN.

SUMMARY

Example embodiments of surgical lighting devices and systems incorporating the same, surgical suction devices and systems incorporating the same, and related methods are described herein. The lighting features and suction features may be employed together or independently. In various embodiments, a suction head or housing is provided that can fit to a handle of an electrosurgical device (e.g., BOVIE), such as at or on a blade portion.

More specifically, the housing may be fit to an insulated portion of the electrosurgery blade (sometimes called its hosel), or it may be fit to the non-insulated portion of the blade, in which case, the housing may incorporate a thermal insulation barrier or be made of a highly temperature resistant polymer (e.g., silicone, TEFLON or PEEK).

The housing can include a light source positioned beyond the distal end of the handle. Lighting may be provided by one or more incandescent light bulbs, light-emitting diodes (LEDs), fiber optic cables or any combination thereof. The type of light source can be selected to provide the optimum amount of illumination of the pocket and the target tissue for dissection immediately distal to the operating portion of the electrosurgical blade. The light source may be balanced to minimize glare for the user while maximizing the visibility within the pocket. Additionally, various types of optical components, including lenses, may be employed to further disperse the light source in various directions as most beneficial to the specific lighting goals. Likewise, the housing can include use of various materials that are either optical clear, translucent, or opaque as for minimization of reflected light to mitigate glare, or further to act as a lens to disperse light in multiple directions.

The housing with the electrosurgery handle forms certain embodiments. Other embodiments concern the housing and its features alone. An embodiment may include a vacuum conduit connected to the housing and/or an associated remotely-located suction device.

Certain embodiments may include a battery pack for the light source. The battery pack may be remote or removed from the housing and electrically connected to the light source through the conduit.

Suction and/or electrical power may be transmitted to the housing via a single or multi-lumen tube or conduit that may be connected to a remote electrical power source. The power source may operate on standard alternating current or direct current via a battery (rechargeable or disposable). The tube or conduit may simply house an electrical wire for such connection or wire conductors may be integrated in the wall of the tube. The tube or conduit may be connected to the electrosurgical device handle using a removable clip.

Methods of use include performing an electrosurgical procedure while illuminating a target site with a light source positioned past a distal end of the electrosurgical handle forming a surgical pocket with the electrosurgical blade. Embodiments of this method include its performance while evacuating smoke from the surgical pocket through an opening in the housing.

Moreover, methods of preparing the subject system for use are contemplated. Namely, a method may be performed in which a housing for light is attached to an electrosurgery handle having a distal end, wherein the light is positioned distal to the distal end of the handle and directed at a blade extending from the electrosurgery handle. The attachment may be made between an electrosurgical blade and the housing. The nature of attachment may be a friction fit. The method may further include attaching provision for suction (or negative pressure/suction itself) to the housing at a battery pack remote from the housing for the light source.

The subject devices, kits in which they are included (with and without assembly), methods of use and manufacture (including assembly of constituent parts) are all included within the scope of the present disclosure. Some aspects of the same are described above, and more detailed description is presented in connection with the figures below.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 4A and 4B are proximal and distal perspective views of another light and/or suction head embodiment.

FIG. 5 is a perspective view comparing the FIGS. 3A-3B and FIGS. 4A-4B embodiments.

DETAILED DESCRIPTION

Figure 1A:
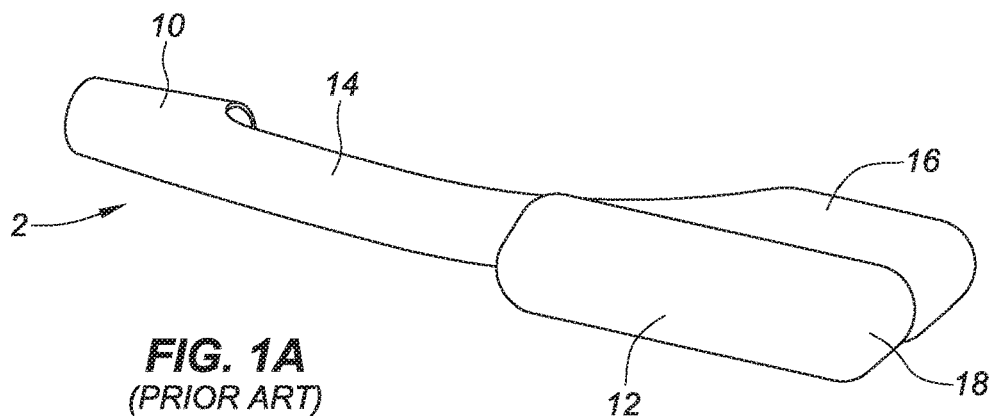
FIGS. 1A-1C are perspective views including the LUMIPEN device referenced above.

Various exemplary embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims made herein.

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description Generally speaking, the components are constructed from biocompatible materials including various metal or metal alloys elastomers and/or plastics (e.g., Silicone, Urethane, Polyurethane, Nylon, HDPE, ABS, PVC, PET). Typical electronics and electrical switches are provided for the light source (e.g., white-light high intensity LED) components. However, other lighting options and components may be provided as commented upon above or otherwise.

In certain embodiments, the subject devices and systems are adapted to account for the fact that the intensity of the light diminishes rapidly (e.g., with the distance squared) from its point of origin. In the LUMIPEN device 2 shown in FIGS. 1A-1C, the point of origin of the light is at the distal end of the handle 100. In the subject embodiments, limited lighting is overcome by placing the light source past the distal end of the handle, thus allowing the maximum intensity of light on the object to be illuminated with the minimal amount of energy at the distance between the source and object are minimized. Further detail discussed in connection with illustrations, below.

First, however, the LUMIPEN features are detailed further for the sake of comparison. Specifically, FIG. 1A shows the LUMIPEN alone. This device 2 includes a distal tube 10, a battery housing 12, an intermediate body 14 and clip sections 16, 18.

Figure 1B:
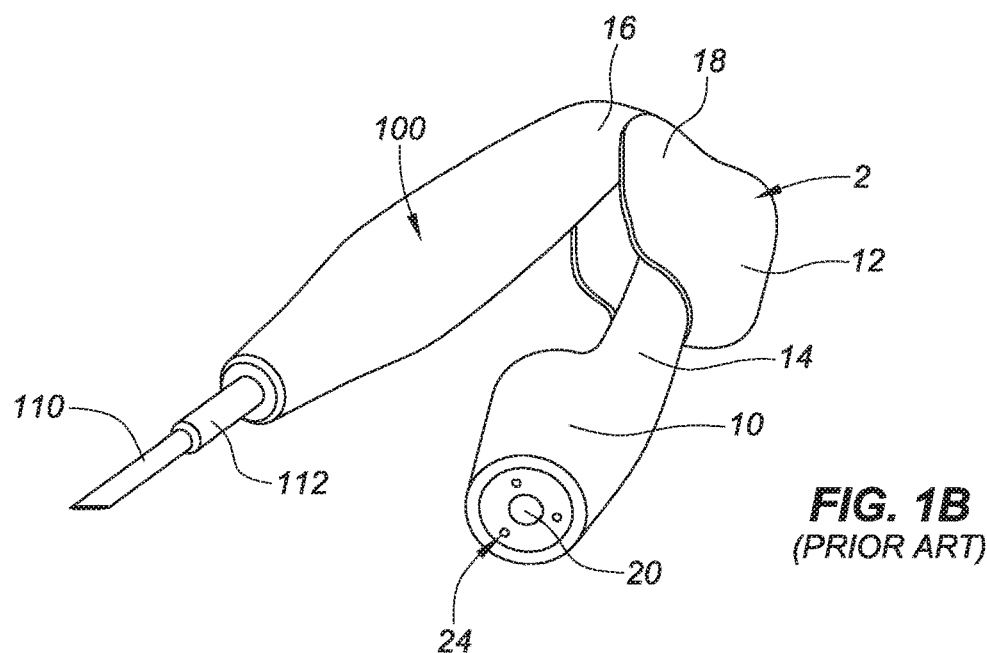
Figure 1C:
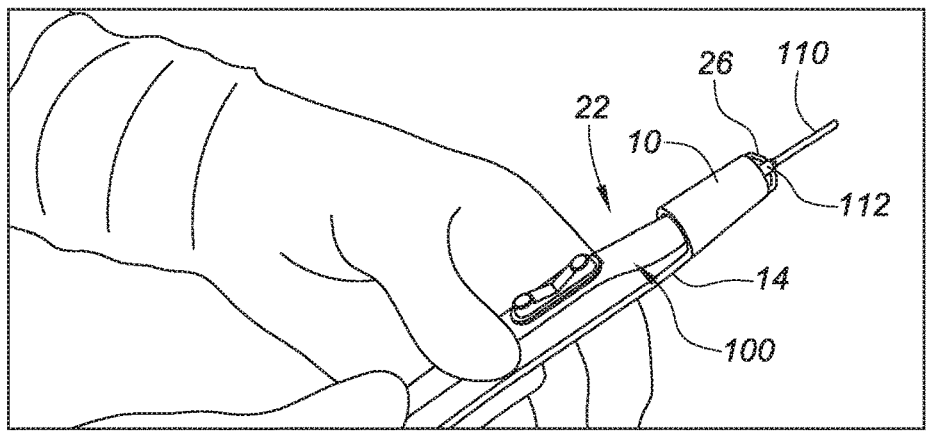

In FIG. 1B, the clip section interaction with the handle of an electrosurgical cutter knife 100 can be seen. Likewise, the electrosurgical knife blade 110 and associated hosel 112 can be seen.

During installation or assembly, blade 110 is passed through tube aperture 20. As such, the assembled system 22 has its LED lights 24 positioned proximal to both the blade 110 and hosel 112 sections. A diffuser or lens cap 26 may cover the LEDs.

In certain subject embodiments, the lights can be positioned adjacent to or coincident with the distal end of the handle for the electrosurgical knife blade. In other embodiments, the light source can be positioned such that part of the light source body itself (e.g., the bulb or diode body, etc.) is distal to the distal end of the handle. In still other embodiments, the entirety of the light source body is positioned distal to the distal end of the handle. Such positioning minimizes the likelihood that an instrument or object will come between the light source and the region (e.g., target or object) to be visualized. Furthermore, the light may always be the same relative distance from the tissue to be illuminated regardless of the length or style of the electrosurgical knife blade.

Figure 2:
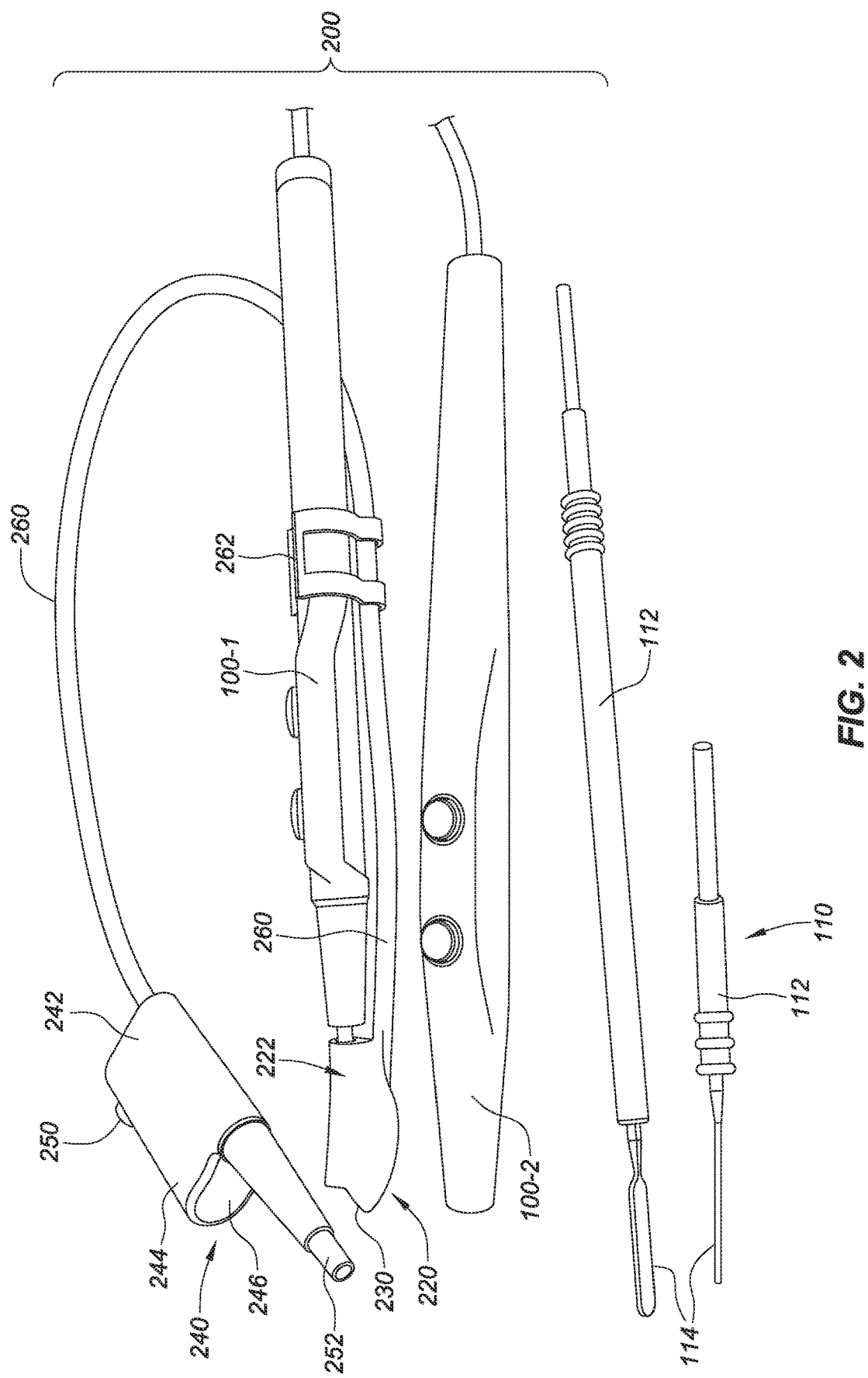
FIG. 2 is an overview of an example embodiment of the subject system components and assembly options.

This relation of elements is shown in FIG. 2 and further discussed in connection with FIG. 3A, below. In FIG. 2, the components of system 200 are shown assembled in connection with an electrosurgical cutter or knife 100-1 (upper) with another electrosurgical knife 100-2 (lower) and blade/hosel components 110/112 independently laid-out or represented.

In system 200, a first housing 220 is connected to a second housing 240 by a flexible conduit 260. A clip 262 holds the conduit to the body of the BOVIE 100.

Housing 220 (alternatively referred to as a suction head) may employ a friction fit between a bore or lumen 222 (positioned centrally or offset) and a distal end of the handle of a medical device, such as an electrosurgical knife 100.

Alternatively, the suction head may be configured to provide a friction fit with a portion of an electrosurgical knife blade insert 100 (such as with the blade's shaft or hosel 112) or the blade tip 114 itself to hold the light and/or suction housing to the electrosurgical knife (or other medical device) handle as far distal as possible.

Notably, different BOVIE blades have different outside dimensions. The housing 220 itself may be elastomeric (e.g., as produced in urethane, polyurethane or silicone) to expand or stretch and accommodate a range of shapes and/or sizes. The bore 222 for fit may be round or oval. It may include compressible fins, bumps, O-rings or other means for space accommodation. These features may be compliant within a hard (e.g., Nylon, ABS or other plastic) housing bore to do the same.

An adjustable friction fit (or other adjustable fit such as actuated by a cammed lever or similar mechanical means) allows for fine longitudinal position control that may be set by a user. The range of adjustment may be between about 2 mm and 5 mm or more. Indeed, the range of adjustment may be the full length of an extended blade or the longest of such blades (e.g., up to a range of motion of 100 mm). Use of a press-on or friction fit also allows for rotational adjustment for the direction of the light source and/or vacuum relative to the blade 114 (whether the blade is paddle-shaped or otherwise configured).

One embodiment uses two Light Emitting Diodes (LEDs). However, one or more than two LEDs may be employed. The number of LEDs or other light source(s), intensity, and projection angles are all variables that may be altered depending on clinical environment. Additionally, the LEDs may be positioned on the same side of the housing where the suction is provided, on both sides, or surrounding the blade from all sides depending on the number of LEDs incorporated or included in the device housing.

Additionally, alternative means of providing light maybe employed such as incandescent bulbs or light provided from a remote location via a fiber optic cable. The light from the fiber optic cable could be generated by an LED set within a battery pack or from some alternate source or location.

Battery pack 240 in system 200 includes upper and lower shell portions 242, 246 across a separation line 246. With the device opened along line 246, a battery may be inserted after run-down if the device is reusable. Otherwise, the system may be intended for one-time use and the pack 240 sealed. In either case, the battery pack may include and on/off button or switch 250, as well as a universal vacuum fitting or interface 252.

Another disadvantage of the LUMIPEN is the negative ergonomic impact of the device in combination with the cautery handle 100. The design of the LUMIPEN clip-on interface is such that the mass of its plastic handle (with included battery housing or pack 16) makes for a less comfortable grip of the surgical instrument. In contrast, the subject embodiments may be configured to minimize negative ergonomic impact by placing battery pack and/or light away from and not on the handle.

Still further, LUMIPEN embodiments include no actual provision for suction. In contrast, the subject embodiments may include such features as shown and described for evacuating smoke and fluid within a/the surgical pocket created by the cautery cutting processes. Specifically, housing 220 includes a vacuum port 230 in fluid communication with conduit 260.

The elimination of smoke may provide for both unobstructed visualization and also provide for a safer work environment by eliminating potential harmful fumes and vapor that may have an adverse biological effect through the inadvertent transmission of viable pathogens and or carcinogens formed as a byproduct of the cauterization of tissue. Another potential advantage of the suction is removal of blood when a blood vessel is breached during the dissection process. Small bleeders most often can be effectively cauterized using an electrosurgical knife if they are relatively dry.

However, due to the blood that is emanating from the breached vessel, the standard BOVIE (a monopolar cautery device) is ineffective. In practice, when a so-called "bleeder" is encountered, the surgeon will put the electrosurgical knife down in exchange for a bipolar cautery device such as a pair of bipolar forceps that can most often be used to effectively staunch the bleeding. Once the bleeding is controlled, the surgeon will then return to using the electrosurgical knife for further dissection. The suction provided by features of the subject embodiment(s) at the tip of the blade of the cautery knife allow a surgeon to effectively staunch the bleeding without resorting to the bipolar instrument, thus saving time and limiting associated blood loss.

Figure 3A:
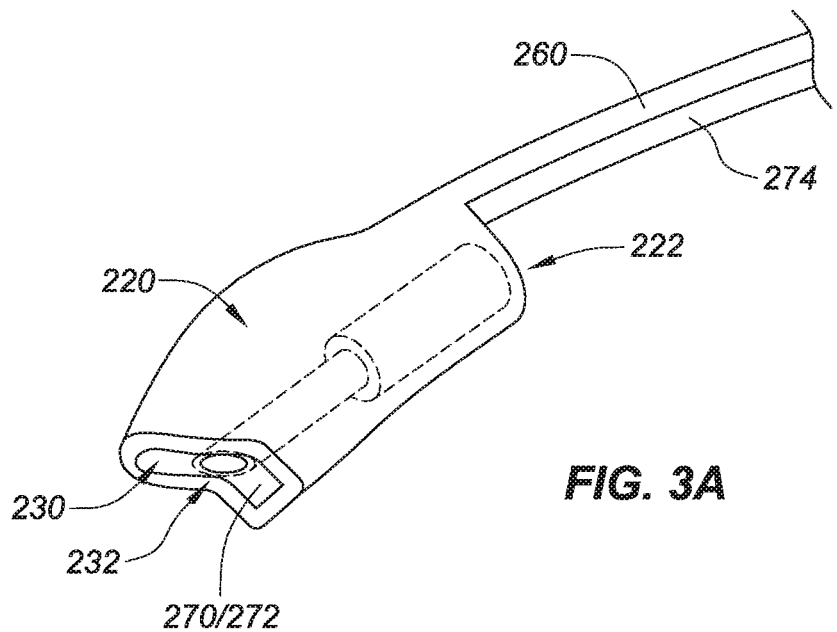
FIGS. 3A and 3B are perspective detail views of a light and/or suction head of an embodiment in a photograph and hidden-line computer model, respectively.
Figure 3B:
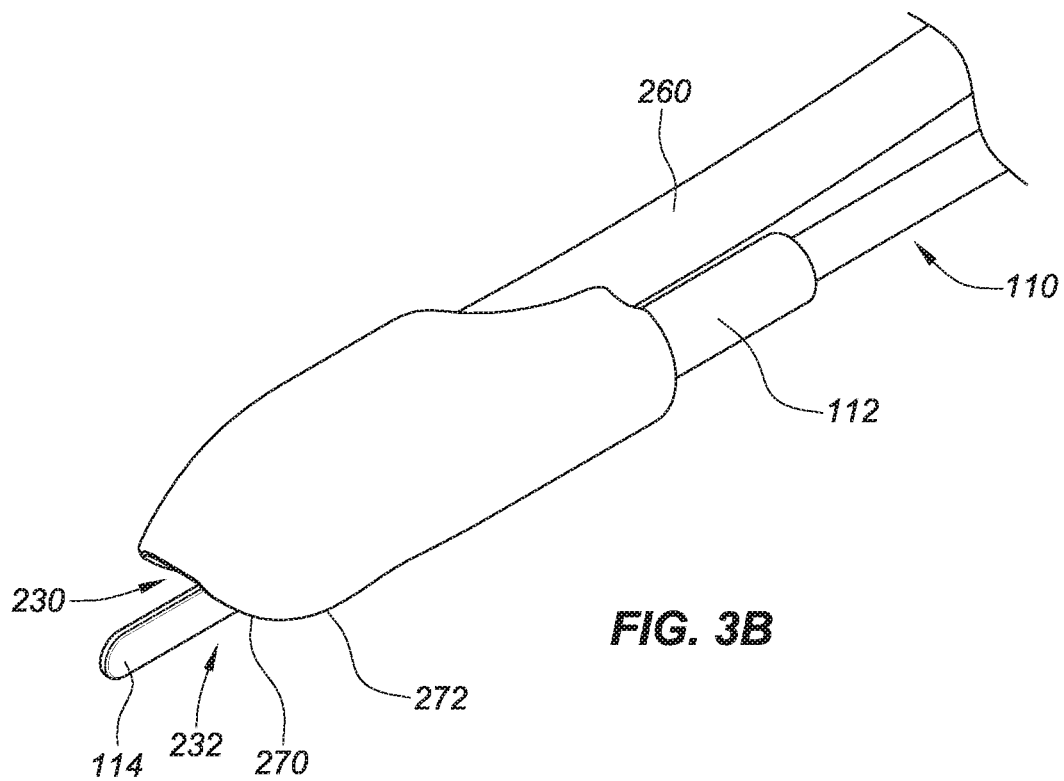

Details of the subject suction and/or lighting head or housing 220 enabling such activity are more easily observed in connection with FIGS. 3A and 3B. Here, the over-arching (literally, with respect to blade tip 114) position of the vacuum port 230 and light position coincident with the blade and past associated electrosurgical knife handle location can be seen. Blade tip 114 pass through a blade aperture or port 232 (see FIG. 3A with the port open and FIG. 3B with the blade in place). The blade shaft or hosel 112 may be held by an elastomeric tube 224 or other interface member received within bore or lumen 222. One or more LED (or other) lights 270, 272 are electrically connected via a wire 274 (optionally housed within conduit 260) with the battery pack.

FIGS. 4A and 4B are proximal and distal perspective views of another light and/or suction housing configuration 280. It may comprise silicone, Nylon, HDPE or be made of another material. Of interest, it offers a one-piece design (as compared the slit-shell design of housing 220 with pieces 220A, 220B in FIG. 5). Other than the insulation 116 upon blade 114 in the configuration shown in FIG. 5, the components are similarly arranged in a complete or working system configuration.

The main differences presented are offered in terms of reduced bulk and opposite-side position of the light. With body 220, the light(s) 270/272 and suction port 230 are across from the blade port 232 in the design. In body 280, the vacuum port and light position are directly adjacent to one another. By having the light positioned and vacuum port on the same side of the blade, the reduction in bulk of the housing provides for an unobstructed view of the cutting blade when being used in a narrow pocket as the angle of visualization decreases dramatically with an increase in the depth of the surgical pocket as well as the narrowing of the incision.

This (the latter) configuration can provide additional benefits in lighting direction and/or intensity as it is directed from "overhead" relative to the blade in use. However, either lighting position may be used. Also, devices including lights in both positions (i.e., high and low relative the blade) are contemplated.

Variations

The subject methods, including methods of use and/or manufacture, may be carried out in any order of the events which is logically possible, as well as any recited order of events. Medical methods may include any of a hospital staff's activities associated with device provision, positioning, re-positioning, and/or operation.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

Though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Accordingly, the breadth of the different inventive embodiments or aspects described herein is not to be limited to the examples provided and/or the subject specification, but rather only by the scope of the issued claim language.

The invention claimed is:

1. An electrosurgery system comprising:
    a detachable housing configured to be pressed onto a standalone electrosurgical cutter at a distal end of a handle of the standalone electrosurgical cutter, wherein the detachable housing comprises a light source positioned at the distal end of the detachable housing, and wherein the detachable housing is configured to be rotatable relative to the electrosurgical cutter such that the light source position rotates relative to a blade of the electrosurgical cutter.

2. The system of claim 1, wherein the detachable housing further comprises a conduit attached to a vacuum port of the housing for suction, wherein the conduit is connected to a suction device.

3. The system of claim 2, wherein the detachable housing further comprises a battery pack, wherein the battery back is remote from the housing and electrically connected to the light source through the conduit.

4. The system of claim 3, wherein the conduit is connected by a fitting included in the battery pack.

5. The system of claim 2, wherein the light source and vacuum port are located on a same side of the electrosurgical blade.

6. The system of claim 5, wherein the vacuum port is closer to the electrosurgical blade than the light source.

7. The system of claim 1, wherein the entirety of the light source is positioned distal to the distal end of the handle.

8. The system of claim 1, wherein the detachable housing is sized to fit only adjacent to a distal end of the handle.

9. The system of claim 8, wherein the detachable housing is less than 50 mm in length.

10. The system of claim 9, wherein the detachable housing is 30 mm in length.

11. The system of claim 1, wherein the detachable housing is connected to the handle by attachment to the blade.

12. The system of claim 11, wherein the detachable housing is attached to a shaft of the blade by a friction fit.

13. The system of claim 12, wherein the friction fit is provided by stretch of a bore in the housing or compression of features included in the bore of the housing.

14. A method of performing an electrosurgical procedure comprising:
    attaching a detachable housing to a standalone electrosurgical cutter, wherein the detachable housing comprises a light source at a distal end of the detachable housing, wherein the detachable housing is configured to be rotatable relative to the electrosurgical cutter such that the light source position rotates relative to a blade of the electrosurgical cutter;
    illuminating a target site with the light source at least partially positioned distal to a distal end of an electrosurgical handle of the standalone electrosurgical cutter; and
    forming a surgical pocket with an electrosurgical blade.

15. The method of claim 14, further comprising evacuating smoke from the surgical pocket through an opening in the detachable housing.

16. The method of claim 15, wherein the light source and the opening are located on a same side of the electrosurgical blade.

17. The method of claim 14, wherein the housing is connected to electrical power and suction at a battery pack separated from the housing by a conduit.

18. A method of preparing an electrosurgical instrument comprising:
    attaching a detachable housing having a light source to a distal end of a standalone electrosurgical cutter, wherein the light source is positioned distal to a distal end of a handle and directed at a blade extending from the electrosurgery handle, and wherein the detachable housing is configured to be rotatable relative to the electrosurgical cutter such that the light source position rotates relative to a blade of the electrosurgical cutter.

19. The method of claim 18, wherein attaching the detachable housing to the distal end of the electrosurgical cutter comprises attaching an electrosurgical blade to the housing.

20. The method of claim 19, wherein attaching the detachable housing to the distal end of the standalone electrosurgical cutter further comprises adjusting a longitudinal position of a friction fit between a bore of the housing and the blade.

21. The method of claim 18, further comprising attaching suction to the detachable housing through a battery pack for the light source, wherein the battery pack is remote from the housing.

* * * * *